United States Patent [19]

Merger et al.

[11] Patent Number: 4,709,072
[45] Date of Patent: Nov. 24, 1987

[54] JOINT PREPARATION OF ETHYLENE CYANOHYDRIN AND ITS ETHERS

[75] Inventors: Franz Merger, Frankenthal; Hans-Martin Hutmacher, Ludwigshafen; Peter Hettinger, Edingen-Neckarhausen; Dieter Voges, Mannheim; Wolfgang Lengsfeld, Limburgerhof, all of Fed. Rep. of Germany

[73] Assignee: BASF Aktiengesellschaft, Ludwigshafen, Fed. Rep. of Germany

[21] Appl. No.: 872,967

[22] Filed: Jun. 11, 1986

[30] Foreign Application Priority Data

Jun. 27, 1985 [DE] Fed. Rep. of Germany ....... 3522906

[51] Int. Cl.$^4$ ................. C07C 121/34; C07C 121/46; C07C 121/75
[52] U.S. Cl. ................... 558/450; 558/451; 558/447
[58] Field of Search ......... 558/450, 451, 447

[56] References Cited

U.S. PATENT DOCUMENTS

| 2,382,036 | 8/1945 | Bruson | 558/450 |
|---|---|---|---|
| 2,393,000 | 1/1946 | Seeger | 558/450 |
| 2,404,164 | 7/1946 | Carpenter | 558/447 |
| 2,448,979 | 9/1948 | Hopff et al. | 558/450 |
| 2,816,130 | 12/1957 | Selcer et al. | 558/450 |
| 3,024,267 | 3/1962 | Howsmon, Jr. | 558/451 |

FOREIGN PATENT DOCUMENTS

| 451809 | 10/1948 | Canada | 558/450 |
|---|---|---|---|
| 1189975 | 4/1965 | Fed. Rep. of Germany | 558/447 |
| 2121325 | 11/1972 | Fed. Rep. of Germany | . |
| 2655794 | 6/1978 | Fed. Rep. of Germany | . |
| 0185550 | 10/1983 | Japan | 558/451 |
| 1007690 | 10/1965 | United Kingdom | . |
| 189828 | 1/1967 | U.S.S.R. | 558/450 |

OTHER PUBLICATIONS

Cyanamid, "The Chemistry of Acrylonitrils", (1959), 2nd ed., pp. 24, 25, 209, 210; pub. by American Cyanamid Co.
Organic Reactions, vol. 5, (1949); Bruson, chapter on "Cyanoethylation", pp. 89, 90, 91, 92, 93.
Abstract of Japan 59196850 (Patent dated 11-8-84) Nitto Chem. Ind.

*Primary Examiner*—Joseph Paul Brust
*Attorney, Agent, or Firm*—John H. Shurtleff

[57] ABSTRACT

Ethylene cyanohydrin (Ia) and its ethers

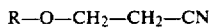

Ib (where R is an organic radical) are prepared jointly by reacting an alcohol R—OH (II) with 2,2'-dicyanodiethyl ether (III) in the presence of a base.

6 Claims, No Drawings

JOINT PREPARATION OF ETHYLENE CYANOHYDRIN AND ITS ETHERS

The present invention relates to a novel process for the preparation of ethylene cyanohydrin (Ia) and at the same time for the preparation of ethers of this compound, of the general formula Ib $$R-O-CH_2-CH_2-CN \qquad \text{Ib}$$

where R is an organic radical, preferaby a hydrocarbon radical of 1 to 6 carbon atoms.

Ethylene cyanohydrin (Ia) and its ethers (Ib) are known to be important intermediates for organic syntheses.

While the ethers are readily obtainable by an addition reaction of an alcohol R—OH (II) with acrylonitrile (cf. for example German Laid-Open Application DOS 2,121,325), the reaction of acrylonitrile with water by a similar method to give Ia presents considerable technical difficulties since this reaction preferentially results in the formation of 2,2'-dicyanodiethyl ether (III)

$$NC-CH_2-CH_2-O-CH_2-CH_2-CN \qquad \text{III}$$

(cf. for example German Published Application DAS 1,189,975), unless a disproportionately large, and hence uneconomical, excess of water is used (Japanese Preliminary Published Application 9196-850).

Although III can be subjected to thermal cleavage in the presence of basic catalyst to give Ia and acrylonitrile (Japanese Preliminary Published Application 83/185 550), considerable effort is required to recover all of the acrylonitrile, which tends to undergo polymerization.

In another process (cf. for example German Laid-Open Application DOS 2,655,794), the direct synthesis of Ia from acrylonitrile and water is carried out in the presence of formaldehyde, byt the latter gives rise to side reactions and furthermore working up the reaction mixture presents technical difficulties owing to the formaldehyde and the unconverted acrylonitrile.

Since there is a danger of considerable losses of acrylonitrile in all these methods, it is primarily an object of the invention to prepare ethylene cyanohydrin in a more economical manner than hitherto. It is a further object of the present invention to obtain the ethers Ib in a technically simple manner.

We have found that this object is achieved by a process for the joint preparation of ethylene cyanohydrin (Ia) and its ethers of the general formula Ib $$R-O-CH_2-CH_2-CN \qquad \text{Ib}$$

where R is an organic radical, wherein an alcohol R—OH (II) is reacted with 2,2'-dicyanodiethyl ether (III) in the presence of a base.

The starting compound III is obtainable in a simple manner by reacting acrylonitrile with water in the presence of a base, for example by the process described in German Published Application DAS 1,189,975. A particular advantage of the novel process is that III need not be isolated from the reaction mixtures obtained in its preparation, these mixtures containing not only III but also water, the base and acrylonitrile; hence, it is preferable to start from such reaction mixtures and to add the alcohol II, especially since the same base can be used in both reaction steps, i.e. the preparation of III and the preparation of Ia and Ib. This procedure is also advisable because conversion of the acrylonitrile need not be complete, since the excess acrylonitrile is converted smoothly to Ib in the reaction step according to the invention.

If III is reacted in the absence of acrylonitrile, Ia and Ib are obtained according to the equation $$NC-CH_2-CH_2-O-CH_2-CH_2-CN \rightarrow HO-CH_2-CH_2-CN + RO-CH_2-CH_2-CN$$

in roughly equal yields, based on III. If acrylonitrile is present, the yield of Ib is increased accordingly if sufficient alcohol is available.

The success of the novel process is in principle independent of the type of alcohol II. Examples of alcohols are:

saturated and unsaturated aliphatic alcohols of 1 to 20, preferably 1 to 6, carbon atoms, such as methanol, ethanol, isopropanol and allyl alcohol, saturated and unsaturated cycloaliphatic alcohols, preferably those possessing 5 or 6 ring members in the cycloaliphatic radical, e.g. cyclohexanol araliphatic alcohols of 7-20 carbon atoms, for example benzyl alcohol and cinnamyl alcohol, and aromatic alcohols, preferably mononuclear or binuclear alcohols, such as phenol, the cresols and the naphthols.

These alcohols may furthermore carry substituents which are inert under the reaction conditions, for example halogen, $C_1$—$C_4$—alkoxy, $C_2$—$C_6$—acyl, tertiary amino groups, nitro or cyano. Finally, it is also possible to use polyhydric alcohols II as starting materials, for example ethylene glycol, the corresponding hydroxyether or bisether being obtained, depending on the ratios.

To achieve complete and sufficiently rapid cleavage of the ether III, it is advisable to use the alcohol II in an amount of 0.5–5 moles per mole of III.

The process for the joint production of ethylene cyanohydrin and 3-methoxypropionitrile by reacting III with methanol is particularly important, since these two compounds are especially important intermediates for organic syntheses.

Bases which are suitable for the base-catalyzed ether cleavage of III are in principle any bases, e.g. hydroxides, carbonates, alcoholates and the salts of weak acids with alkali metals and alkaline earth metals, NaOH and KOH being preferred. Other suitable compounds are tertiary amines, such as triethylamine and pyridine, and basic phase-transfer catalysts, such as quaternary ammonium and phosphonium bases, e.g. benzyltrimethylammonium hydroxide and -phosphonium hydroxide. The basic phase-transfer catalysts are used especially when they are already present in the mixture obtained in the reaction of acrylonitrile with water to give III, and such mixtures are employed for the reaction according to the invention.

The bases can be used in principle in any amount, since this merely affects the reaction rate. Good results are obtained as a rule using 0.1–50, in particular 0.5–10 mg, meq per mole of III.

The novel reaction takes place at an adequate rate at as low as about 40° C., and higher temperatures than 140° C. are as a rule of no futher advantage. The reaction is preferably carried out at about 50°–120° C., and it may be necessary to employ superatmospheric pressure.

For the preparation of III from acrylonitrile and water, temperatures of 20°-100° C., preferably 50°-80° C., are advisable.

In other respects, the novel process does not have any special features in terms of process engineering, so that further information in this regard can be dispensed with. The same applies to the working up of the reaction mixtures obtained.

EXAMPLE

Preparation of ethylene cyanohydrin and its methyl ether

A mixture of 168 g (1.36 moles) of 2,2'-biscyanoethyl ether (III), 46 g (0.9 mole) of acrylonitrile, 12 g (0.17 mole) of ethylene cyanohydrin, 27 g (1.46 moles) of water, 0.32 g (0.008 mole) of NaOH, 0.4 g (0.002 mole) of benzyltrimethylammonium hydroxide and 16 g of high boilers, as obtained in the reaction of 212 g (4 moles) of acrylonitrile with 58 g (3.2 moles) of water and the stated amounts of the bases at 65°-70° C. after the reaction time of 1 hour, was stirred with 640 g (20 moles) of methanol for 3 hours at 70° C.

Analysis of the reaction mixture by gas chromatography showed that III was virtually completely converted to equal molar amounts of ethylene cyanohydrin and 3-methoxypropionitrile. Thus, about 40% of ethylene cyanohydrin and about 48% of its methyl ether were formed, the percentages being based on the acrylonitrile initially employed.

We claim:

1. A process for the joint preparation of ethylene cyanohydrin of the formula $$HO-CH_2-CH_2-CN$$

and its ether of the formula $$R-O-CH_2-Ch_2-CN$$

wherein R has the meaning given below, which comprises:
    reacting at 40° to 140° C. and in the presence of a base
    (A) an alcohol R—OH (II) where R denotes the residue of a saturated or unsaturated hydrocarbyl aliphatic alcohol of from 1 to 6 carbon atoms and the same substituted with a halogen, hydroxy, $C_1$-$C_4$-alkoxy or nitro group, or an alcohol R—OH (II) selected from the group consisting of cyclohexanol, benzyl alcohol, cinnamyl alcohol, phenol, cresol or naphthol, with
    (B) the reaction mixture which is obtained by the reaction of acrylonitrile and water in the presence of a base and which contains 2,2'-dicyanodiethyl ether of the formula $$NC-CH_2-CH_2-O-CH_2-CH_2-CN \qquad (III),$$

as the reaction product, the total amount of base for the reaction of (A) with (B) being 0.1 to 50 meq per mole of the ether (III) and said alcohol R-Ho (II) being used in an amount of 0.5 to 5 moles per mole of the ether (III).

2. A process as claimed in claim 1 wherein the alcohol (II) is selected from the group consisting of methanol, ethanol, isopropanol and allyl alcohol.

3. A process as claimed in claim 1 wherein the alcohol (II) is methanol.

4. A process as claimed in claim 1 wherein the base is selected from the class consisting of hydroxides, carbonates, alcoholates, and the salts of weak acids with alkali metals and alkaline earth metals.

5. A process as claimed in claim 1 wherein the base is selected from the group consisting of NaOH and KOH.

6. A process as claimed in claim 3 wherein the base is selected from the group consisting of NaOH and KOH.

* * * * *

UNITED STATES PATENT AND TRADEMARK OFFICE
CERTIFICATE OF CORRECTION

PATENT NO. : 4,709,072

DATED : November 24, 1987

INVENTOR(S) : Franz Merger, Hans-Martin Hutmacher, Peter Hettinger, Dieter Voges and Wolfgang Lengsfeld It is certified that error appears in the above-identified patent and that said Letters Patent is hereby corrected as shown below:

Claim 1, after line 2, to the right of the first formula: insert -- (Ia) --.

Claim 1, after line 3 (disregarding the first formula), the second formula should read: -- $R-O-CH_2-CH_2-CN$ --.

To the right of the second formula, insert -- (Ib) --.

Claim 1, next to the last line: change "R-Ho" to -- R-OH --.

Signed and Sealed this

Fourteenth Day of June, 1988

Attest:

DONALD J. QUIGG

Attesting Officer     Commissioner of Patents and Trademarks